United States Patent
Levy

(10) Patent No.: US 7,611,480 B2
(45) Date of Patent: Nov. 3, 2009

(54) GASTROINTESTINAL BIOREACTOR

(76) Inventor: Mark M. Levy, Etzion 34, Raanana 43563 (IL)

( * ) Notice: Subject to any disclaimer, the term of this patent is extended or adjusted under 35 U.S.C. 154(b) by 651 days.

(21) Appl. No.: 10/422,091

(22) Filed: Apr. 24, 2003

(65) Prior Publication Data

US 2004/0213825 A1 Oct. 28, 2004

(51) Int. Cl.
*B01L 11/00* (2006.01)
*G01N 33/53* (2006.01)
*C12M 1/00* (2006.01)
*C12M 1/12* (2006.01)
*A61B 1/00* (2006.01)
*A61B 5/00* (2006.01)
*A61N 1/30* (2006.01)
*A61M 1/00* (2006.01)
*A61M 5/178* (2006.01)
*A61M 3/00* (2006.01)
*A61M 31/00* (2006.01)
*A61M 37/00* (2006.01)

(52) U.S. Cl. .................. 604/27; 422/101; 435/7.1; 435/289.1; 435/297.1; 435/297.2; 600/103; 600/117; 600/309; 600/573; 600/582; 604/19; 604/31; 604/36; 604/43; 604/57; 604/85

(58) Field of Classification Search ............... 422/101; 435/7.1, 289.1, 297.1, 297.2; 600/103, 117, 600/309, 573, 582; 604/19, 27, 31, 36, 43, 604/57, 85

See application file for complete search history.

(56) References Cited

U.S. PATENT DOCUMENTS

| | | | |
|---|---|---|---|
| 4,077,407 A | | 3/1978 | Theeuwes et al. |
| 4,207,890 A | * | 6/1980 | Mamajek et al. ............ 424/473 |
| 4,453,929 A | * | 6/1984 | Silverman et al. ........... 604/518 |
| 4,925,446 A | * | 5/1990 | Garay et al. ........... 604/103.02 |
| 4,976,858 A | * | 12/1990 | Kadoya ...................... 210/496 |

(Continued)

FOREIGN PATENT DOCUMENTS

EP  1 128 579  8/2001

(Continued)

*Primary Examiner*—Mark L Shibuya
*Assistant Examiner*—Jacqueline Diramio
(74) *Attorney, Agent, or Firm*—Dekel Patent Ltd; David Klein

(57) ABSTRACT

An in-vivo bioreactor device producing a dialysis effect by acting within the gastrointestinal tract for the removal of undesirable concentrated intestinal or blood substances or metabolites is disclosed. The ingestible device is comprised of a body wall that surrounds an internal compartment. Along the wall of the shell are openings located around the periphery that allow bodily fluids to enter and exit device. The wall of the device is comprised in whole or at least in part of materials that are impermeable to the passage of external fluids and maintains its physical and chemical integrity in the environment of use during its activity. Semi-permeable membranes located either internally or externally of the device are able to withstand all physiological temperatures and pH and act in a similar manner to dialysis membranes that are used for the separation of substances in suspensions, solutions, tissue cultures, etc. Treatment materials, including fixing agents that act in a similar manner to ion exchange resins, biologically active agents including proteins, enzymes, or live bacteria, and medicinal agents, can be placed in the internal cavity of the device for the treatment of various conditions.

16 Claims, 4 Drawing Sheets

U.S. PATENT DOCUMENTS

| | | |
|---|---|---|
| 5,604,531 A | 2/1997 | Iddan et al. |
| 5,925,030 A * | 7/1999 | Gross et al. ............... 604/890.1 |
| 6,168,948 B1 | 1/2001 | Anderson et al. |
| 6,428,469 B1 | 8/2002 | Iddan et al. |
| 2001/0017851 A1 | 8/2001 | Yamaguchi et al. |
| 2002/0132226 A1* | 9/2002 | Nair et al. ...................... 435/4 |
| 2005/0100535 A1* | 5/2005 | Farmer et al. ............ 424/93.46 |
| 2005/0147559 A1* | 7/2005 | von Alten .................... 424/9.1 |
| 2006/0004255 A1* | 1/2006 | Iddan et al. .................. 600/160 |

FOREIGN PATENT DOCUMENTS

| | | |
|---|---|---|
| JP | 404138128 A * | 5/1992 |
| WO | WO 95/07578 | 3/1995 |
| WO | WO 99/44066 * | 9/1999 |
| WO | WO 00/64373 | 11/2000 |
| WO | WO 01/89162 | 11/2001 |
| WO | WO 02/102243 * | 12/2002 |

\* cited by examiner

GASTROINTESTINAL BIOREACTOR

TECHNICAL FIELD

The present invention relates generally to a gastrointestinal bioreactor and methods of treating patients to remove undesirable substances from the body. More particularly, the invention is directed to an in-vivo gastrointestinal bioreactor having a body member containing materials that remove or treat undesirable intestinal, blood substances, or metabolites through the action of passive or active transmission of gastrointestinal (GI) fluids through the device.

BACKGROUND OF THE INVENTION

For various reasons, including diet, substance use, illness, injury or surgery, patients may require supplementation of their natural body functions in order to remove fluid-containing dissolvable waste products from their blood or gastrointestinal (GI) fluids. Several procedures known for this purpose are dialysis, hemodialysis, hemofiltration and hemodiafiltration. For example, dialysis is used to remove soluble waste and solvent from blood; hemofiltration is used to remove plasma water from blood; and hemodiafiltration is used to remove both unwanted solute (soluble waste) and plasma water from blood.

It is also known that a number of metabolic toxins such as mercaptans, free fatty acids, and conjugated bilirubin and endotoxins are completely bound with proteins in the bloodstream. Because of the size of the molecules and the strong body interaction of the protein toxin complex, it is difficult or impossible to select and remove from blood toxins bound to albumin by traditional blood purification methods such as hemodialysis. Hemoperfusion is a blood purification method that works in conjunction with activated carbon or iron exchange resins that absorb materials including the protein-bound toxins.

It is well known that individuals that are diagnosed with chronic renal insufficiency can be treated with the aid of dialysis. Substances that are usually eliminated in the urine are removed with the assistance of a filtering device that contains a semipermeable membrane. However, during the course of the long term, hemodialysis complications can occur that include chronic accumulation of inorganic phosphate in dialysis patients. Phosphate body agents can be administered orally and used as therapeutic agents, which are intended to prevent the reabsorption of food phosphates in the gastrointestinal tract.

Another treatment procedure that has been used is peritoneal dialysis, wherein a sterile saline solution is injected into the peritoneal cavity and remains there for a period of time. During this period, some toxic substances may cross the peritoneum that serves as a natural membrane, and are thereafter removed from the body along with the solution. This procedure is semi-invasive and carries a risk of infection. Also, such a procedure is not suitable for the removal of a variety of substances, and may not be suitable for all patients.

A disadvantage of various of the above-mentioned treatments is that the biological fluids of the patient have to be transferred from the body, circulated through an exterior treating device, and then returning the biological fluids back to the patient. These treatments are typically done in a medical setting such as a hospital, and require the patient to travel to and from the hospital where the procedure is performed. This process can be time-consuming and disruptive to the normal activity of the daily life of the patient.

Devices are also known, which deliver a drug agent to an environment of use, are known. These devices are made with a wall formed of a material that is permeable to an external fluid and substantially impermeable to the beneficial agent. The wall is known to surround a compartment that contains the agent and a passageway through the wall for dispensing the agent.

A known group of polymers called non-absorbed polymers are designed to operate in the gastrointestinal tract and selectively bind specific target molecules. These polymers are orally administered in capsule or tablet form, pass through the stomach and into the intestines where targeted molecules bind with the polymer, pass through the intestinal tract, and are excreted from the body.

The disadvantage of the orally administered treatments resides in the fact that they are typically designed to treat an individual ailment. A separate treatment must be ingested in order to effectively treat each diagnosed ailment. Furthermore, since these treatments are dispersed within the GI tract and not absorbed by the body, there is a chance that some of the agents can remain in the body for extended periods of time.

The need exists for an in-vivo bioreactor having the capability of removing undesirable intestinal, blood substances, or metabolites, which avoids the deficiencies of the prior devices and methods.

SUMMARY OF THE INVENTION

It is an object of the present invention to provide an in-vivo gastrointestinal bioreactor. The system comprises housing, which can pass through the entire digestive tract and enter the gastrointestinal tract to treat a patient, such as by removal of concentrated intestinal or blood substances or metabolites, producing a treatment and/or dialysis effect. Such undesired substances are retained inside of the device until it is excreted from the body. Alternatively, the device may be used to treat a patient by reaction of constituents within the GI tract or to dispense agents into the GI tract.

Another object of the invention is to provide a device having a swallowable, non-digestible housing having an external shell and defining an internal cavity. The shell may be formed of a membrane material or a separate membrane may be located relative to the internal cavity to selectively allow predetermined constituents of a fluid to pass therethrough. A treatment material is provided within the internal cavity to selectively treat predetermined constituents within the cavity. The membrane may also enable the passage of predetermined fluidic constituents out of the cavity.

Yet another object of the invention is to provide a method of treating a patient to remove toxins from the gastrointestinal tract with an in-vivo bioreactor by providing a swallowable, non-digestible housing having an external shell and defining at least one internal cavity. A membrane selectively allows predetermined constituents of a fluid to pass into the internal cavity. A treatment material is located within the internal cavity that treats or binds predetermined constituents within the cavity. The membrane also enables the passage of predetermined fluidic constituents out of the cavity.

A further object of the present invention is to provide a method of biochemically processing materials located in the gastrointestinal tract with an in-vivo bioreactor by providing a swallowable, non-digestible housing having an external shell and defining at least one internal cavity containing a treatment material therein. A membrane selectively allows predetermined constituents of a fluid to pass into the cavity, and the treatment material located within the internal cavity biochemically processes predetermined constituents within the fluid. The membrane enables the passage of processed fluidic constituents out of the cavity. The housing is ingested and travels to the gastrointestinal tract where gastrointestinal fluids, blood, and metabolites located within the gastrointestinal tract are passed through the housing. Toxic substances located within the gastrointestinal fluids or blood are then converted to a less toxic or less active form by biological factors including bacteria, enzymes, or proteins that are housed within the bioreactor and then returned to the gastrointestinal tract. Once the housing passes through gastrointestinal tract, it is excreted through natural ways using peristaltic motion of the gastrointestinal tract.

Yet another object of the invention is to provide a device having a swallowable, non-digestible housing having an external shell and defining at least one internal cavity, wherein the internal cavity is sectioned into at least two compartments. There is a membrane located relative to the internal cavity to selectively allow predetermined constituents of a fluid to pass therethrough. A treatment material within the internal cavity selectively treats the predetermined constituents within the cavity and the membrane enables the passage of predetermined fluidic constituents out of the cavity.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

In the drawings, which are not drawn to scale, are set forth to illustrate various embodiments of the invention, the figures are as follows.

DETAILED DESCRIPTION OF THE INVENTION

Figure 1:
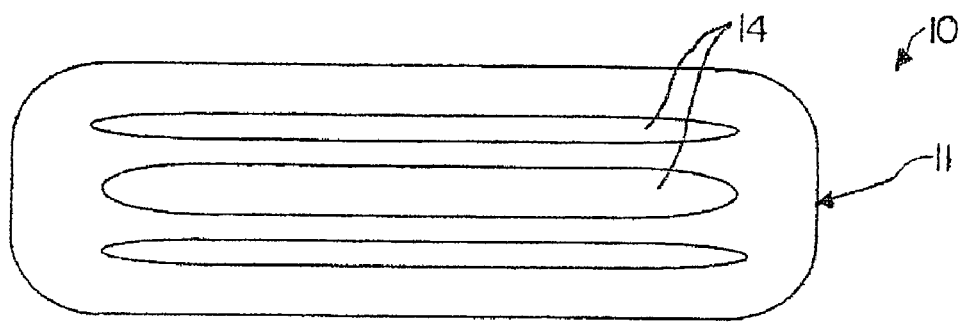
FIG. 1 is a plan view of an in-vivo bioreactor device according to an embodiment of the present invention.

The ingestible in-vivo bioreactor device of the present invention is generally shown at 10 in FIG. 1. The device 10 may be used for removal from the blood and other fluids in the gastrointestinal tract, of predetermined agents or materials found therein. The device 10 is designed to operate within the GI tract due to its rich vascular network and length, which will provide a long dwell time and contact between the device and the gastrointestinal content as well as the capillary-rich bowel mucosa. In such an embodiment, the removal of materials substantially produces the inverse effect of physiological gastrointestinal absorption. As an example, the device 10 may be used to remove undesirably high physiological substances, creatinine, uric acid, hepatic toxic metabolites, electrolytes, toxins or heavy metals, alcohol metabolites, drugs and glucose. The device may also facilitate the binding of substances inside the gastrointestinal tract that have recently been ingested as a form to avoid absorbable substances already ingested in excess including alcohol, sugars, fats, and working potentially as a diet supplement. The device may be used for treatment of diseases or the like, where the concentration of a substance is too high in the blood and is removed through the system via the gastrointestinal tract. Hepatic or renal insufficiency or other problems associated with high concentration of certain materials can be treated. The device may also be used to avoid possible over or under desired ingestion of given substances with food.

In normal conditions, the absorption of nutrients from the bowels content to the blood is done through the capillary network. The device 10 may be used to prevent certain materials from entering the bloodstream through this network, effectively providing a dialysis-type of function. The above materials are examples of such substances that may be filtered by the device, and retained within the device to be ultimately expelled from the body through normal peristaltic motion of the gastrointestinal tract. In an embodiment of a treatment method, the ingestion of multiple devices 10 may increase the chances of reducing the blood concentration of an undesirable substance without dialysis and/or in a short amount of time as compared to other treatment procedures. For example, retention enemas using Kayexalate resin have been sued to lower potassium levels within the body. Kayexalate, a form of sodium polystyrene sulfanate, is a catyon-exchange resin prepared in the sodium phase, and lowers serum potassium within the blood. Although effective, such treatment may take hours to days and it has been found that treatment with this drug alone may be insufficient to rapidly correct sever hyperkalemia for example. Using the device 10 of the present invention, the treatment for such condition may utilize one or more of the devices 10 in a manner to remove potassium from the body in a more effective and efficient manner this prior treatment procedure. Similarly, the device 10 may be used to treat conditions such as lead poisoning, wherein lead would be removed from the body such as by use of a material which can separate heavy metals from liquid media. For example, a resin material produced by Dow Chemical, referred to as Dowex resins, can be used for separation of lead or other heavy metals from bodily fluids. Other natural materials, such as algae or other natural extracts are also contemplated. As should be evident, the removal of a variety of other substances from body fluids within the GI tract using one or more devices 10 may provide an alternative to present treatments for a variety of conditions or materials within the body. The manner by which such materials are removed from the body using the device 10 will be described in more detail hereafter.

Figure 2:
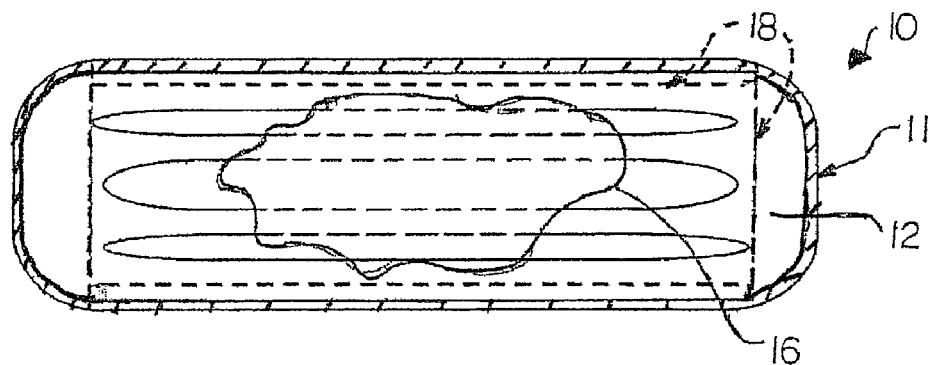
FIG. 2 is a cross-sectional view of an embodiment of the device of FIG. 1 illustrating an inner membrane housing a treatment medium in accordance with the present invention.

Turning now to the drawings in detail, which are various examples of an in-vivo bioreactor device of the present invention. Reference is now made to FIGS. 1 and 2, which shows the schematic structure of the bioreactor device 10. The device 10 is comprised of an outer housing or shell 11 that forms at least one internal compartment 12. The shell 11 may have openings 14 around the periphery or ends that allow bodily fluids to enter and exit device 10. The device 10 may have a capsule-like shape as shown or may have any other shape as desired. The openings 14 can be located and dimensioned in any desired manner to allow desired flow of fluids into the internal compartment 12, and in this embodiment, extend longitudinally around the entire periphery. The shell 11 may be comprised in whole or part of materials to form a wall that is impermeable to the passage of an external fluid, and maintains its physical and chemical integrity in the environment of use during its activity. Alternatively, the shell 11 may be constructed of a material which is permeable or semipermeable to bodily fluid, which may negate the need for openings 14.

Materials that are used to form the shell 11 of device 10 include, but not limited to, polyurethane, polystyrene, plastics, polymers, silicon or other synthetic material. New shape memory polymers are also within the scope of device 10. Metallic materials including stainless steel and nitinol may be considered. The shell 11 may be hard or semi-flexible, and can be of fixed dimensions or may be selectively expandable in one or more directions. Forming shell 11 of a material so that it can expand to a degree within the GI tract during use, may allow more of desired constituents to be removed from the body.

The shell may be alternatively constructed of a porous material, designed to allow passage of certain fluidic constituents, so as to act as a membrane in accordance with the invention. As used herein, "membrane" serves the function of allowing the passage of predetermined fluidic constituents, while preventing the transmission of other constituents therethrough. If the shell 11 is constructed of a material which does not serve as a membrane, a separate membrane 18 may be provided. The at least one internal cavity 12 may house at least one treatment material 16 located within an internal membrane 18. In embodiments wherein a treatment material 16 is utilized, the membrane 18 may simply contain the material 16 in the cavity 12. If the housing 11 is formed of a porous membrane material, the treating material 16 may be linked to a molecule which will not pass through the housing material, while allowing other fluidic constituents into and out of the internal cavity 12. A more detailed description of various membranes and treatment materials in accordance with the invention appears later in the specification.

Figure 3:
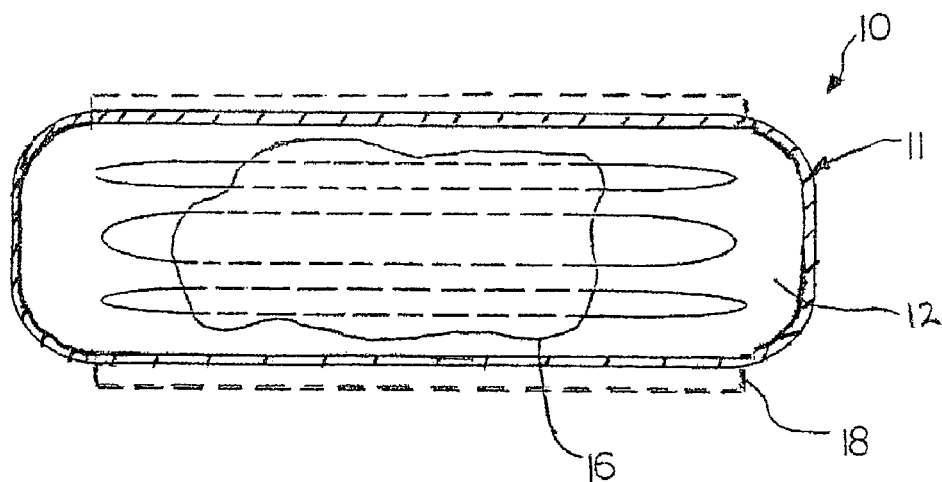
FIG. 3 is a cross-sectional view of an alternative embodiment of the device in FIG. 1 illustrating an outer membrane and an internal housing in accordance with the present invention.

As an alternative to providing membrane 18 internal to cavity 12, an outer membrane 18 may cover the shell 11 or openings 14 of device 10, as shown in FIG. 3. The internal cavity 12 may similarly house treatment materials 16.

Figure 3A:
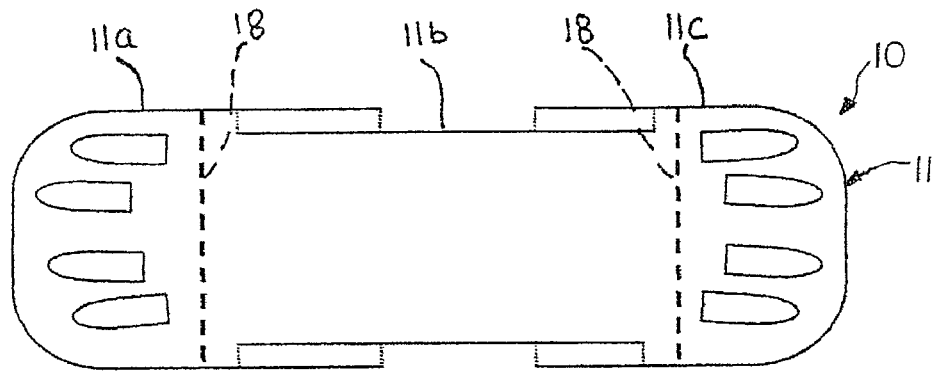
FIG. 3A is a plan view of an alternate embodiment of the bioreactor device having a variable dimension housing.

The in-vivo bioreactor device 10 of FIGS. 1-3 may act inside the gastrointestinal tract for the removal of undesired highly concentrated intestinal or blood substances or metabolites, producing a dialysis effect. While device 10 can have various conventional shapes and sizes, a typical size of the shell 11 is up to 11 millimeters in diameter and up to 30 millimeters long. The device 10 could also be sized to facilitate use with children, or otherwise as desired. Shell 11 may be made from expandable materials or expansion of shell 11 facilitated by its construction. In FIG. 3A, the shell 11 is formed from a series of sections formed into a telescoping mechanism, which allows selective expansion of the housing. In such a configuration, housing sections 11a and 11c are telescopically engaged with a central section 11b. As an example, each of the housing sections may include retaining surfaces 13 which engage one another at a fully extended position. In this way, sections 11a and 11c are moveable longitudinally relative to section 11b, for selective expansion of the housing 11. Alternatively, sections 11a and 11c may be interconnected by a central section 11b formed in an accordion configuration as an example. Other structures to allow selective expansion of housing 11 are also contemplated. It is also possible to utilize a material such as nitinol, a shape memory alloy that may be programmed to expand like a stent inside the gastrointestinal tract due to a change in body temperature.

In the foregoing embodiments, the membrane 18 (whether formed by housing or as a separate member) may be semipermeable to allow the selective transmission of various constituents therethrough. The membrane 18 is able to withstand all physiological temperatures or pH and may have a variable range of porosity. Suitable membranes include dialysis membranes that are typically used in chemistry for separation of substances on suspensions, solutions, columns, tissue cultures, etc. These membranes can be produced from various materials including regenerated cellulose, a mixture of chemically pure cellulostic esters and a polyvinylidine fluoride, which is a flouropolymer, like Teflon, and is resistant to most organic solvents, as well as, corrosive aqueous solutions. These membranes can also be chosen based on their chemical compatibility such that the membranes will be stable in various chemical environments.

Incorporation of a separate membrane 18 can be accomplished in various manners. In one embodiment, the membrane 18 freely moves throughout internal cavity 12 of the device 10, such as in the embodiment of FIG. 2. Alternatively, membrane 18 is secured to the shell 11 to cover the openings 14. The membrane is positioned inside the internal cavity 12 to contain a treatment material therein. The membrane 18 may be similar to a bag containing a substance inside, or may be one or more pieces of membrane material to cover openings 14. If membrane 18 is attached to shell 11 of device 10, again the function of maintaining material within the cavity 12 is performed in any desired configuration.

In an embodiment, the device 10 is again used to remove constituents from bodily fluids within the GI tract. A treatment material 16 to serve as a fixing agent may be any material capable of fixing predetermined constituents within a fluid material. As mentioned previously, various compounds are contemplated within the scope of the invention, to fix certain substances so as to cause effective filtering of the substance from the bodily fluids. The semi-permeable membrane 18 allows the desired materials to pass therethrough so as to interact with the treatment material within the internal cavity 12. The treatment material 16 may be of any known character suitable for insertion within the device 10, which can selectively bind certain substances in association therewith. Examples of these types of agents include resins, charcoal, hyaluronic acid, or synthetic or natural gels. These fixing or dialysis agents may act like ion exchange resins that are capable of removing undesired bodily substances, or may simply filter and trap substances.

Alternatively, the semi-permeable membrane 18 itself may be used to retain certain substances therewith as the bodily fluid passes through the membrane 18. A combination of membrane characteristics as well as use of a treatment material 16 within device 10 may also enable various materials to be removed or enhance removal of certain substances.

Figure 4:
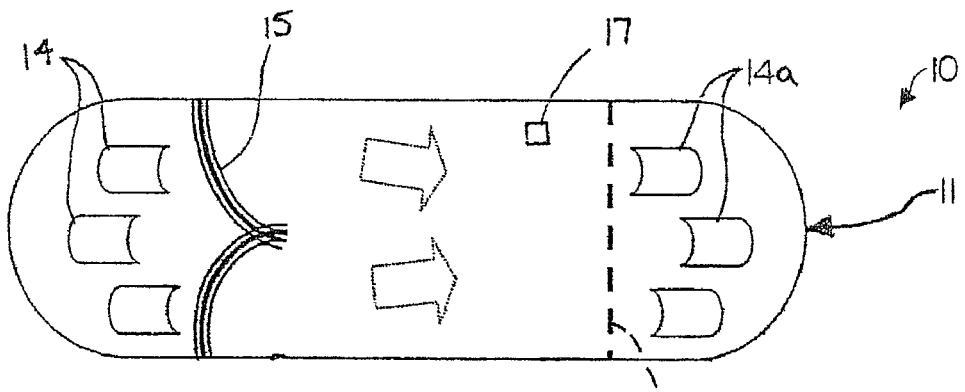
FIG. 4 is a somewhat schematic cross-sectional view of a further embodiment of the device, which does not utilize a treatment material.
Figure 4A:
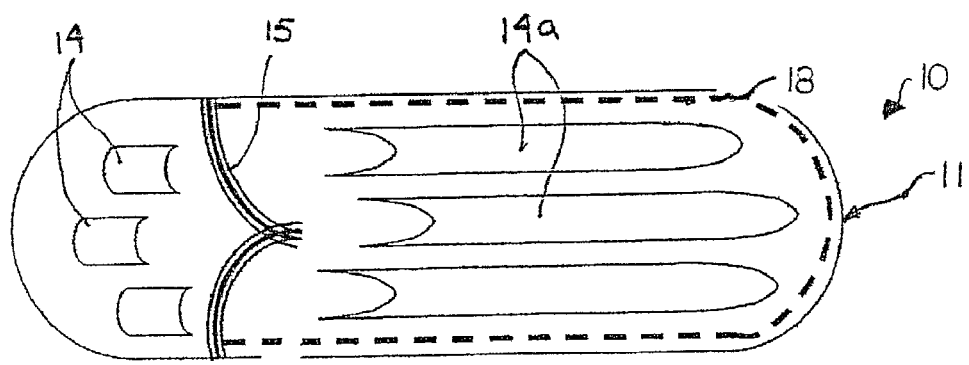
FIG. 4A is a somewhat schematic cross-sectional view of an embodiment of the device of FIG. 4.

In a further embodiment, such as shown in FIG. 4, the shell 11 includes inlet openings 14, which allow the ingress of fluidic constituents within the GI tract, and a one-way valve 15, which allows these constituents into an internal cavity within shell 11. The fluid passes through a membrane 18 and out exit openings 14a, with membrane 18 filtering desired substances from the fluidic constituents. In this embodiment, no treatment material is required to remove desired constituents. An alternative embodiment is shown in FIG. 4A, wherein membrane 18 extends on the interior of shell 11 past one-way valve 15. Greater flow of fluid and larger surface area of membrane 18 may facilitate removal of desired substances.

In the treatment of patients, it may also be desirable to enable tracking of the device 10 as it passes through the GI tract or other portions of the body. A suitable marking device 17 may be used as an indicator for detection by various non-invasive imaging modalities, such as x-ray, MRI or other imaging techniques. If desired, the indicator may also be triggered by certain activity of the device 10 within the GI tract, such as by reactivity with predetermined constituents, an indication of treatment or treatment progress, or the like.

In another embodiment of the present invention, the in-vivo bioreactor 10 may contain a treatment material for biochemically interacting with the bodily fluids. The treatment material may comprise active agents such as chemicals, pharmaceuticals, live bacteria, enzymes, proteins or other biological factors that are capable of converting one substance to a less toxic or less active structure, or for introducing a substance into the GI tract. The converted materials pass through device 10 and are released to the gastrointestinal tract in a modified form. Enzymes like lactase for lactase intolerance and other enzymes for intestinal conditions used as digestive complements including lipase, diastase, pancreatin, enzymes to degrade gluten, etc., are provided in a state that may ensure or enhance activity when placed into the gastrointestinal tract in device 10. Useful bacteria like lactobacillus, acidophilus can be delivered to a specific area in the gastrointestinal tract and use may be made of a particular membrane to selectively introduce such agents. Other bacteria capable of being contained in the device 10 are those that selectively allow introduction of products of their metabolism into the gastrointestinal tract in a controlled fashion due to the specific characteristics of the membrane. Other active agents may be considered for use in device 10, such as agents useful for gene therapies or other therapeutic agents. Other materials for converting a substance into a less toxic or less active structure are contemplated.

In another embodiment the treatment agents can be retained within an envelope of a degradable substance, such as similar to an oral medication capsule that is composed of gelatin, glycerin, egg shell, starch, edible oil, fat or vegetable oil, water soluble fiber or a mixture of these materials. Such a secondary housing can assure the stability of the agents when they are inserted inside internal cavity 12 of device 10. Once device 10 is ingested, the degradable capsule is digested in the stomach or beginning of the small bowel, thus liberating the treatment agents to interact with the bodily fluids.

The housing is ingested and travels to the gastrointestinal tract where gastrointestinal fluids, blood, and metabolites located within the gastrointestinal tract are passed through the housing. The toxins located within the gastrointestinal fluids, blood or the metabolites are filtered through the membrane. The toxins are retained in the membrane and are isolated from the gastrointestinal fluids or the blood. Once the housing passes through gastrointestinal tract, it is excreted through natural ways using peristaltic motion of the gastrointestinal tract.

Figure 5:
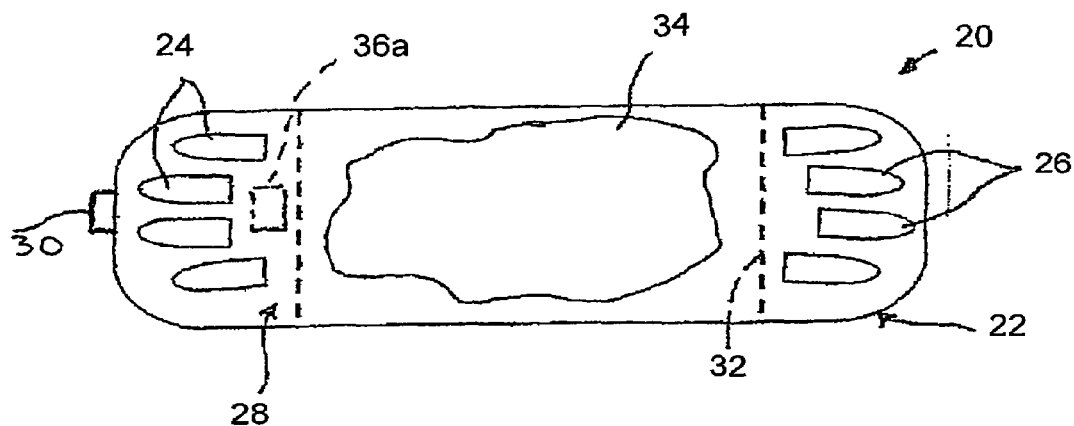
FIG. 5. is a somewhat schematic cross-sectional view an embodiment illustrating use of a pump or motor facilitating the active transmission of fluids through the device in accordance with the present invention.

A further embodiment of the invention is shown in FIG. 5, which is directed to a device 20, which may serve a function similar to the embodiments already described above, but includes active transmission of bodily fluids therethrough. As seen in FIG. 5, the device 20 may include a housing 22, which may again be formed of a rigid or semi-flexible shell that can tolerate all physiological degrees of PH or temperature to be encountered within the GI tract. In this embodiment, the shell 22 may be configured to have an ingress opening 24 and an egress opening 26, which may be disposed on opposing ends of the device 20 as shown, or in another suitable fashion for the ingress of bodily fluids into the internal cavity 28 formed by shell 22. For the active transmission of fluids through the device 20, a pump or motor 30 located relative to the internal cavity 28 of device 20 actively transmits bodily fluids from one end of the device 20 through opening 24 to the other end through opening 26. The active transmission of bodily fluids with the assistance of pump or motor 30 through internal cavity 28 promotes flow of the bodily fluids to pass through the internal membrane 32, into contact the treatment material 34, and out of the housing 22. The pump or motor 30 could also be used in conjunction with passive transmission of bodily fluids into internal cavity 28 of device 20 through openings in the housing, such as in prior embodiments having openings 14, such as seen in FIG. 1. The pump or motor 30 can be located on the periphery of shell 22 of device 20, as seen in FIG. 5, or may be located internal to the device as shown at 30a. In this embodiment, the pump or motor 30 could provide a force to propel, rotate or otherwise cause motion of device 20 inside the body to increase the flow of bodily fluids into and through the internal cavity 28 of device 20. Alternate locations of pump or motor 30 are near opening 24 to increase the flow into internal cavity 28 and/or opening 26 for the outward flow through device 20.

Figure 6:
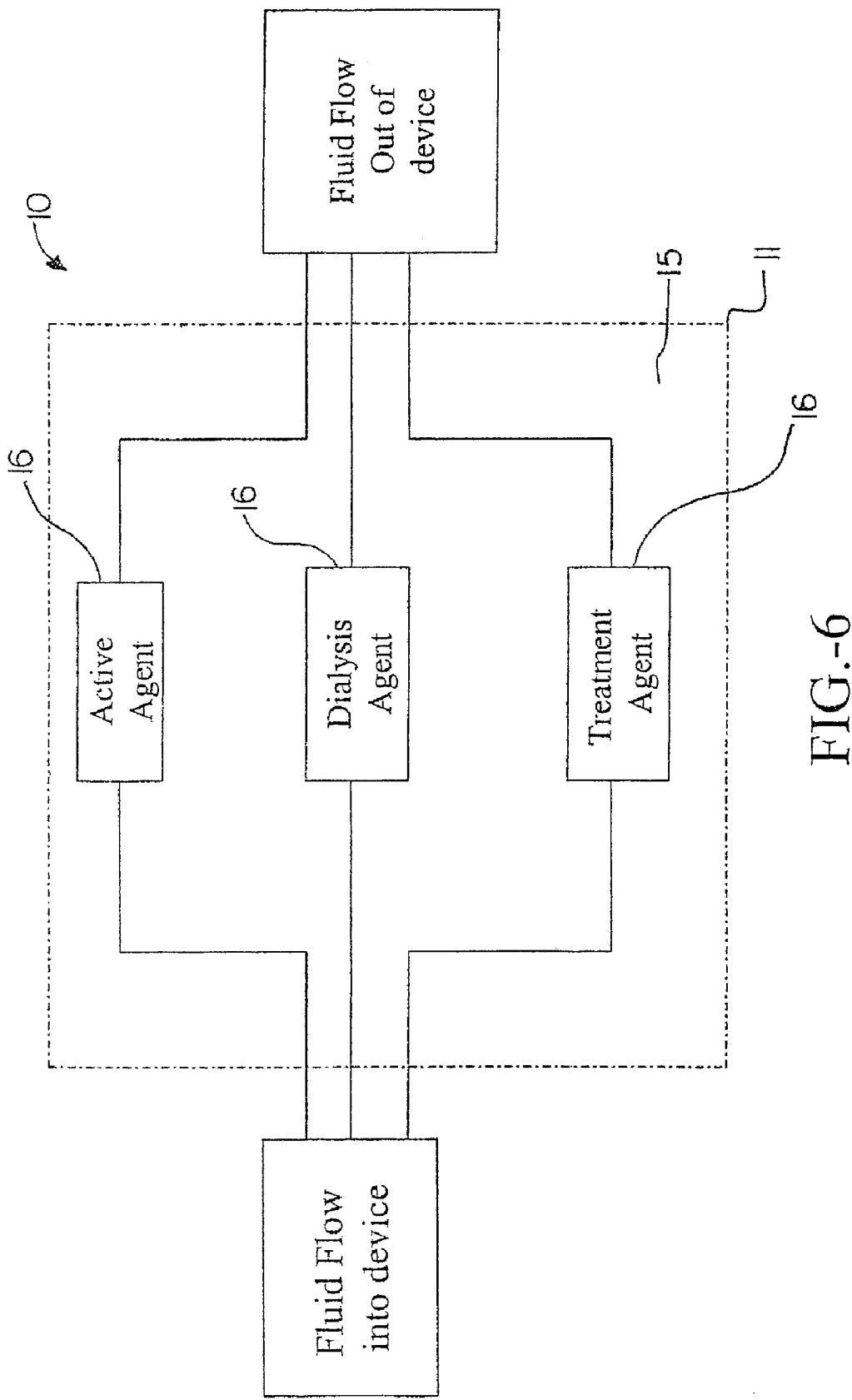
FIG. 6 is a block diagram illustration showing various treatment methods using a treatment medium in accordance with the present invention.

Turning to FIG. 6, illustrated in block diagram format, a method of using an ingestible in-vivo bioreactor device 10 or 20 is shown where bodily fluids flow through the shell 11 of device 10 via the material of shell itself or through openings located on the periphery or ends of shell 11 and into internal cavity 15. Inside internal cavity 15 are located treatment materials 16 that include fixing or dialysis agents, active agents, and other possible treatment agents. As previously mentioned, the fixing or dialysis agents may be a membrane material and/or a fixing agent positioned in the cavity 15. Treatment materials 16 process, convert, and fix undesirable and highly concentrated substances found in the gastrointestinal tract. The treated bodily fluids then flow out of the device 10 back into the gastrointestinal tract.

Figure 7:
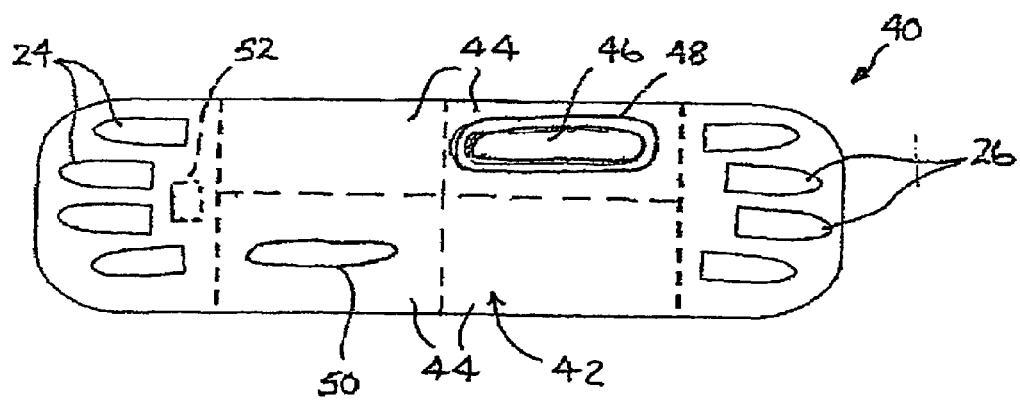
FIG. 7 is somewhat schematic cross-sectional view of another embodiment of the device illustrating the compartmentalization of treatment materials within the device in accordance with the present invention.

A further embodiment of the device according to the invention is shown in FIG. 7. The device 40 may have similar characteristics to previous embodiment, but may include an internal cavity 42 having multiple compartments 44 which contain treatment material 46 therein. Individual internal membranes 48 may be used with each treatment material or compartment 44 or a single membrane may be used similarly to that described previously. Alternatively, a degradable housing 50 containing treatment materials 46 could be used. A pump or motor 52 may be used to facilitate the flow of bodily fluids through device 40.

It is also contemplated in the invention that the device 10 may include or carry constituents which are released and digested within the GI tract or digestive tract. The device 10 may be configured to include portions that are selectively digested at certain levels within the GI tract for the release of predetermined agents or desired treatment process. As an example, a portion of the shell 11 may be configured to be digested at a predetermined region of the GI tract for selective treatment of fluidic constituents within this region. Alternatively, the exterior shell 11 may be configured to be digestible, while a treating substance and membrane interior to the device will be released for interaction with the fluidic constituents in the GI tract.

Although the present invention has been described with reference to the various embodiments thereof, various modifications and adaptations are considered to be within the scope of the invention and are contemplated thereby. The scope and protection afforded under the patent is therefore only limited according to the appended claims.

The invention claimed is:

1. An in-vivo bioreactor device comprising:
a swallowable, at least partly non-digestible housing having an external shell and defining at least one internal cavity, at least one membrane provided relative to the at least one internal cavity to selectively allow predetermined constituents of a fluid from the gastrointestinal tract to pass through said at least one membrane while other fluidic constituents of the fluid from the gastrointestinal tract do not pass through said at least one membrane; wherein said predetermined constituents from the gastrointestinal tract that have passed through the at least one membrane are retained in said internal cavity so as to selectively remove said predetermined constituents from the gastrointestinal tract upon introduction of the device into the gastrointestinal tract, wherein said shell has at least one inlet opening on one side of said at least one membrane and at least one exit opening on an opposite side of said at least one membrane that allow bodily fluids to respectively enter and exit the device while the device is in the body, said openings extending longitudinally on a periphery of said shell.

2. The device of claim 1, wherein said external shell is constructed of an expandable material.

3. The device of claim 1, further comprising at least one treatment material within the at least one internal cavity, the treatment material selectively treating predetermined constituents within the at least one cavity and the at least one membrane enabling the passage of predetermined fluidic constituents out of the at least one cavity.

4. The device of claim 1, wherein the at least one membrane is provided by the housing material, having characteristics to allow passage of predetermined fluidic constituents while filtering other constituents.

5. The device of claim 1, wherein the at least one membrane is provided by a separate membrane material positioned relative to the housing to allow passage of a fluid therethrough.

6. The device of claim 1, wherein the at least one membrane filters materials selected from the group consisting of toxins, creatine, uric acid, hepatic toxic metabolites, alcohol metabolites, electrolytes, therapeutic or medicinal agents, detergents, renal metabolites, poisonous substances and heavy metals or combinations thereof from gastrointestinal fluids, and blood located within the gastrointestinal tract.

7. The device of claim 1, further comprising a pump to cause gastrointestinal fluids to pass through the at least one membrane.

8. The device of claim 3, wherein the treatment material binds certain materials therewith, so as to remove the materials from the body upon expulsion of the device from the body.

9. The device of claim 3, wherein the treatment materials are selected from the group consisting of binding agents, ion-exchange resins, charcoal, hyaluronic acid, natural extracts synthetic or natural gels or combinations thereof 10. The device of claim 3, wherein the treatment materials are materials that convert predetermined substances to a less toxic or a less active configuration.

11. The device of claim 10, wherein the treatment materials are selected from the group consisting of proteins, enzymes, live bacteria or combinations thereof, and convened substances pass through the device and are returned to the gastrointestinal tract.

12. The device of claim 1, wherein the at least one internal cavity houses a pump to process gastrointestinal fluids and expel the processed fluids back to the gastrointestinal tract actively or passively through a valve or a membrane located within the at least one internal cavity.

13. The device of claim 2, wherein the expandable material is selectively expandable in one or more directions.

14. The device of claim 1, wherein the device further comprises a marker for identifying the device in the body using non-invasive imaging processes.

15. The device of claim 1, wherein the at least one internal cavity is sectioned into at least two compartments.

16. The device of claim 1, wherein said membrane has a variable range of porosity.

\* \* \* \* \*